(12) United States Patent
McPherson et al.

(10) Patent No.: US 7,431,230 B2
(45) Date of Patent: Oct. 7, 2008

(54) APPARATUS AND METHOD FOR BONE MORSELIZATION FOR SURGICAL GRAFTING

(75) Inventors: Cameron N. McPherson, Fort Worth, TX (US); Larry D. Estes, North Richland Hills, TX (US); Scott A. Singer, Watauga, TX (US)

(73) Assignee: Medtronic PS Medical, Inc., Goleta, CA (US)

( * ) Notice: Subject to any disclaimer, the term of this patent is extended or adjusted under 35 U.S.C. 154(b) by 597 days.

(21) Appl. No.: 11/081,230

(22) Filed: Mar. 16, 2005

(65) Prior Publication Data
US 2006/0226267 A1    Oct. 12, 2006

(51) Int. Cl.
*B02C 19/00* (2006.01)

(52) U.S. Cl. ............ 241/30; 241/169; 241/169.2; 241/283

(58) Field of Classification Search ........... 241/283, 241/270, 169, 169.2, 30; 606/80, 102
See application file for complete search history.

(56) References Cited

U.S. PATENT DOCUMENTS

| | | | | |
|---|---|---|---|---|
| 3,066,350 A | * | 12/1962 | Quiring | 452/141 |
| 3,761,026 A | * | 9/1973 | Rohmer | 241/199.12 |
| 3,856,219 A | * | 12/1974 | Stayton et al. | 241/263 |
| 4,209,135 A | * | 6/1980 | Starks | 241/46.17 |
| 4,706,897 A | | 11/1987 | Moeller | |
| 5,607,269 A | | 3/1997 | Dowd et al. | |
| 5,653,173 A | | 8/1997 | Fischer | |
| 5,730,372 A | * | 3/1998 | Bradley | 241/29 |
| 5,769,853 A | | 6/1998 | Quetin | |
| 5,918,821 A | | 7/1999 | Grooms et al. | |
| 6,142,997 A | | 11/2000 | Michelson | |
| 6,162,227 A | | 12/2000 | Eckhardt et al. | |
| 6,287,312 B1 | | 9/2001 | Clokie et al. | |
| 6,318,651 B1 | | 11/2001 | Spiering | |
| 6,402,070 B1 | | 6/2002 | Ishida et al. | |
| 7,083,623 B2 | * | 8/2006 | Michelson | 606/80 |
| 2004/0155132 A1 | | 8/2004 | McPherson et al. | |

FOREIGN PATENT DOCUMENTS

DE    9000094 U    1/1991

* cited by examiner

*Primary Examiner*—Mark Rosenbaum
(74) *Attorney, Agent, or Firm*—Haynes and Boone, LLP

(57) ABSTRACT

A bone morselization apparatus and method according to which a cutter bit is mounted to a casing containing a motor; and the casing is manually grasped and positioned over a plurality of bone segments. When the motor is activated, the cutter bit reciprocates and the bone segments are impacted by the cutter bit to morselize the segments.

20 Claims, 1 Drawing Sheet

APPARATUS AND METHOD FOR BONE MORSELIZATION FOR SURGICAL GRAFTING

BACKGROUND

This invention relates to an apparatus and method for fracturing bones into smaller bone particles, or morsels, for use in surgical procedures such as surgical grafting for bone augmentation or repair.

Surgeons, particularly when dealing with spinal fusion, oral/maxillofacial, orthopedic, periodontal, and implant applications, often perform autologous bone grafts using autogenous bone that is ground into relatively small particles, or morsels. For example, in a spinal fusion application, the surgeon can use bone from the patient's mandibular symphsis or ramus, then grind the bone and utilize the bone morsels in the fusion procedure. Such procedures reduce the costs of surgery compared with other products, such as hydroxy appetite (HA) granules, processed coral, or freeze-dried bone.

Bones are often morselized by bone mills having a cutting blade with a plurality of teeth. However these devices are relatively inefficient since they require a significant amount of mechanical force as well as time to complete the morselization process. Also, there is often a significant loss of bone within the bone grinders themselves, since chunks of bone become wedged between adjacent teeth of the cutting blade and/or between the teeth and the milling apparatus. Other designs of bone mills involve rasp tools and are very complicated and expensive.

Therefore, what is needed is an apparatus and method for bone morselization which avoid the above problems.

All patents listed in Table 1 are hereby incorporated by reference herein in their respective entities. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

TABLE 1

| Patent/Publication No. | Patented/Published Date | Inventor |
| --- | --- | --- |
| 6,318,651 | Nov. 20, 2001 | Spiering |
| 6,287,312 | Sep. 11, 2001 | Clokie et al. |
| 6,162,227 | Dec. 19, 2000 | Eckhardt et al. |
| 5,918,821 | Jul. 6, 1999 | Grooms et al. |
| 5,769,853 | Jun. 23, 1998 | Quetin |
| 5,607,269 | Mar. 4, 1997 | Dowd et al. |
| 4,706,897 | Nov. 17, 1987 | Moeller |
| 4,252,282 | Feb. 24, 1981 | Vermeulen, et al. |
| 6,142,997 | Nov. 7, 2000 | Michelson |
| 5,653,713 | Aug. 5, 1997 | Fischer |

SUMMARY

According to an embodiment of the invention, a bone-morselization apparatus is provided that includes a vertically reciprocating cutter bit having a plurality of cutting elements. As a result, when the blade is reciprocated, the cutting elements impact and fracture bone segments into multiple morsels.

Various embodiments of the invention discussed below may possess one or more of the above features and advantages, or provide one or more solutions to the above problems existing in the prior art.

DETAILED DESCRIPTION OF THE PREFERRED EMBODIMENT

Figure 1:
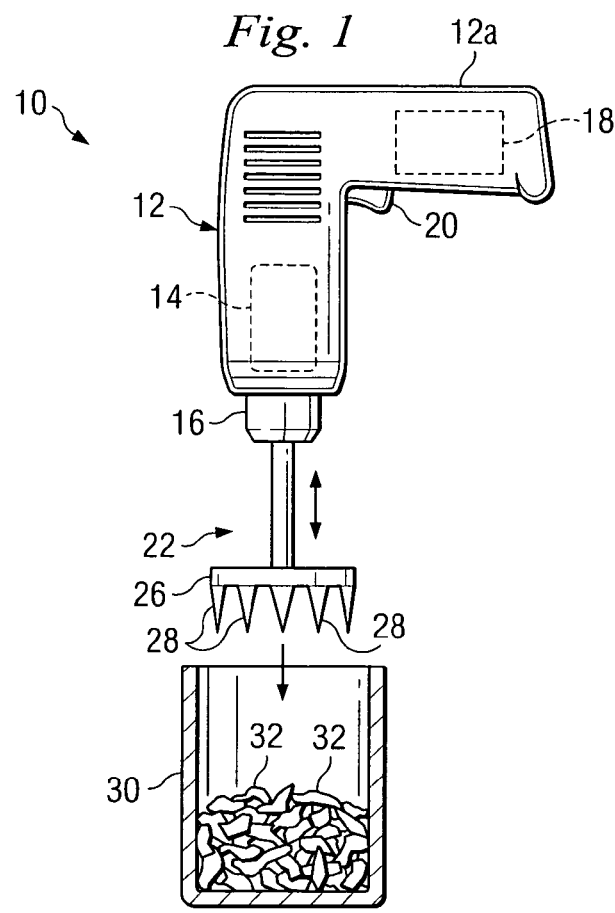
FIG. 1 is a partial sectional/partial elevational view of an apparatus according to an embodiment of the invention.

Referring to FIG. 1 of the drawings, the reference numeral 10 refers, in general, to an apparatus for morselizing bones into smaller bone particles, or morsels, for use in surgical grafting. The apparatus 10 includes a substantially L-shaped casing 12 having a manually gripable handle 12a and containing a motor 14. In one embodiment, the motor 14 is a conventional variable speed, brushless, dc motor adapted to produce a reciprocal output.

A collet 16 is located at one end of the casing 12 and is adapted to be coupled between the output shaft (not shown) of the motor 14 and the shaft of a cutter bit to be described.

The motor 14 is adapted to reciprocate its output shaft and is powered by a conventional rechargeable battery pack 18 disposed in the handle 12a or, alternately, by house current through an electric cable (not shown) attached to the casing 12.

A trigger 20 is provided that extends outwardly from the handle 12a and is adapted to control the speed of the motor 14 and/or turn it on or off. In this context, it is understood that proper electronics (not shown) can be provided in the casing to facilitate control of the motor 14. In the event the motor 14 is not turned on and off by the trigger 20, a separate switch (not shown) for this purpose can be provided on the casing 12.

Figure 2:
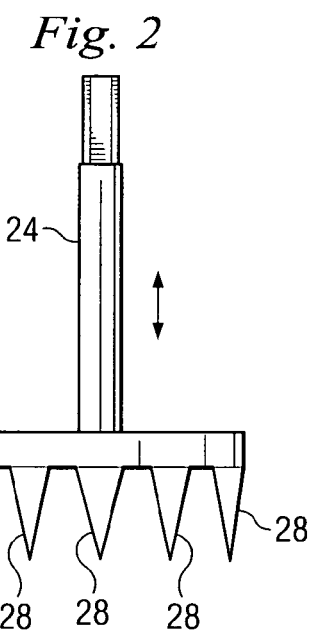
FIG. 2 is an enlarged elevational view of the tool in the embodiment of FIG. 1.

Referring to FIGS. 1 and 2, a cutter bit 22 is provided that consists of a shaft 24 having one end portion that extends in, and is lockingly engaged by, the collet 16. A circular base member 26 extends from the other end of the shaft 24 and a plurality of cutting elements 28 extend from the lower surface of the base member 26. In the example shown, there are five cutting elements 28, each having a substantially triangular cross-section that tapers inwardly in a direction from the base member 26, with the taper being such that a relatively sharp point is formed at the distal end of each cutting element 28. In one embodiment, the shaft 24, the base member 26, and the cutting elements 28 are formed integrally.

It is understood that the design of the casing 12 (FIG. 1) and the collet 16 are such that the collet 16 is coupled between the output shaft of the motor 14 and the shaft 24 of the cutter bit 22, and that reciprocal movement of the motor shaft in response to activation of the motor 14 causes corresponding reciprocation of the cutter bit 22.

A vessel 30, having an open end, is provided for receiving a plurality of bone segments 32. After the segments 32 are placed in the vessel 30, the handle 12a is manually grasped and the cutter bit 22 positioned over the vessel 30 with the shaft 24 extending substantially vertically. The motor 14 is turned on causing reciprocal movement of the bit 22, and the bit is lowered into the vessel 30 until the cutting elements 28 impact and morselize the bone segments 32.

Figure 3:
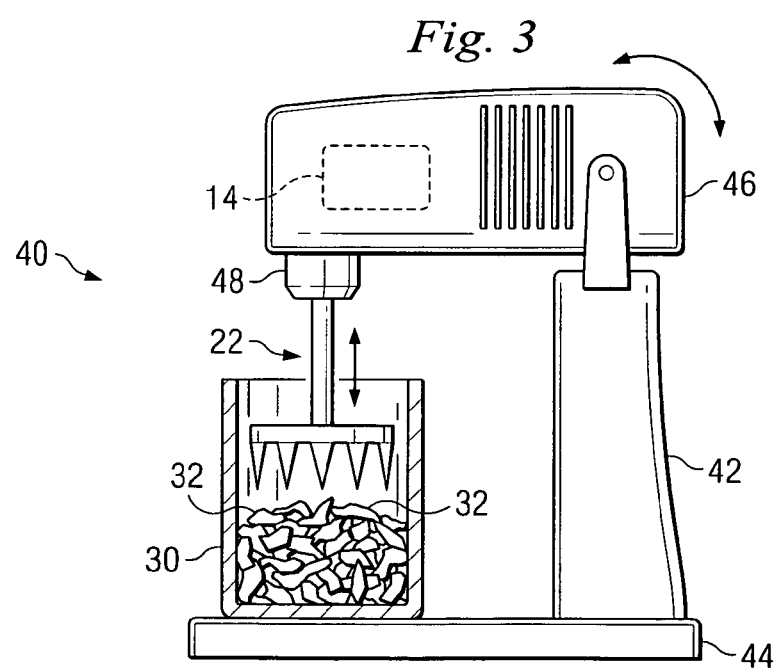
FIG. 3 is a view similar to that of FIG. 1 but depicting another embodiment of the invention.

According to the embodiment of FIG. 3, the reference numeral 40 refers, in general, to an apparatus for morselizing bone segments according to another embodiment of the invention. The apparatus 40 includes a substantially vertically-extending pedestal 42 mounted on a base member 44. An arm 46 is pivotally mounted to the pedestal 42 for movement between the substantially horizontal position shown and a position at a slight angle to the horizontal.

The reciprocal motor 14 of the previous embodiment is mounted in the arm 46, and a collet 48 extends from the lower surface of the distal end portion of the arm 46 and is coupled to the output shaft of the motor 14 for reciprocation therewith. An end portion of the cutter bit 22 of the previous embodiment is mounted in the collet 48 with its shaft 24 extending substantially vertically.

It is understood that the motor 14 can be connected to a source of house current by a cable (not shown) connected to the pedestal 42, and that an on-off switch and a speed control can be provided on the arm 46 or the pedestal 42 to control the motor 14. In the latter context, electronics can also be provided in the arm 46, the pedestal 42, or the base member 44 to facilitate this control. It is also understood that the cable for house current, the on-off switch, or the speed control can be supplied, independently of each other, on any combination of the arm 46, the pedestal 42, or the base member 44.

As in the previous embodiment, it is understood that the design is such that the collet 48 is coupled between the output shaft of the motor 14 and the shaft 24 of the cutter bit 22 in a manner to allow reciprocation of the cutter bit 22 in response to activation of the motor 14.

The vessel 30 of the previous embodiment, with a plurality of segments 32 contained therein, is positioned on the base member 44 directly under the cutter bit 22. If necessary, the arm 46 can be pivoted so that its distal end portion moves upwardly to allow the vessel 30 to be placed in position. The arm 46 is then pivoted back to its substantially horizontal position shown in FIG. 3 and is activated to cause reciprocal movement of the bit 22 so that the cutting elements 28 impact and morselize the bone segments 32.

In both of the above embodiments, the term "morselize" is used in a broad sense and is intended to cover fracturing, cracking, comminuting, milling, pulverizing, hacking, rupturing, cutting, disintegrating, all other forms of morselization, or any combination thereof.

Variations

It is understood that variations can be made in the above without departing from the scope of the invention. For example, the design of the cutter bit 22, including the design of the elements 28, can be varied within the scope of the invention. Also, mechanisms other than the collets 16 and 48 can be used to lockingly engage the cutter bit 22 while permitting reciprocal movement of the bit. Further, the shape of the casing 12, the arm 46 and the pedestal 42, as well as the pivotal mounting of the arm 46 to the pedestal 42, can be varied. Still further, the motor 14 in the embodiment of FIG. 1 can be disposed in the handle 12a, and, in the embodiment of FIG. 3, it can be disposed in the pedestal 42. Moreover, the vessel 30 can be eliminated or replaced by a container of a different design. Also, the particular type of medical procedure utilizing the morselized bone in accordance with the above can be varied.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to the particular design of the casing 12, and the support assembly consisting of the pedestal 42, the base 44, and the arm 46, but may find further application with other types of casings and assemblies.

The present invention further includes within its scope methods of making and using the apparatus described hereinabove. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An apparatus for morselizing bone segments, the apparatus comprising:
a casing;
a motor disposed in the casing and having a reciprocal output; and
a cutter bit having a longitudinally extending shaft coupled to the motor so as to reciprocate when driven by the motor to impact and morselize the segments, the cutter bit also having a circular base member fixed relative to the shaft, the circular base member having a lower surface defining a plane substantially normal to the longitudinally extending shaft with a plurality of cutting elements protruding therefrom,
the reciprocal output from the motor reciprocating both the shaft and the circular base member.

2. The apparatus of claim 1 wherein the cutter elements taper to a point in a direction from the base member.

3. The apparatus of claim 1 wherein the motor is a variable speed brushless dc motor configured to produce the reciprocal output.

4. The apparatus of claim 1 further comprising a collet mounted to the casing and coupled between the motor and the cutter bit to reciprocate the cutter bit upon activation of the motor.

5. The apparatus of claim 1 wherein the casing comprises a handle that can be manually grasped to position the cutter bit over the segments.

6. The apparatus of claim 1, wherein the cutter elements taper to a point in a direction from the base member, the cutter elements at the base member being spaced apart from each other along the lower surface of the base member.

7. The apparatus of claim 1, wherein the cutter elements have a greatest width adjacent the base member and taper in a direction from the base member, the cutter elements being spaced apart from each other such that a portion of the lower surface is disposed between adjacent cutter elements.

8. The apparatus of claim 1, wherein the cutter elements have a greatest width adjacent the base member and a height from the lower surface of the base member, the height being a distance about twice the greatest width.

9. An apparatus for morselizing bone segments, the apparatus comprising:
a pedestal;
an arm extending from the pedestal;
a motor disposed in the pedestal or the arm and having a reciprocal output; and
a cutter bit having a longitudinally extending shaft coupled to the motor so as to reciprocate when driven by the motor to impact and morselize the segments, the cutter bit also having a circular base member fixed relative to the shaft, the circular base member having a lower surface defining a plane substantially normal to the longitudinally extending shaft with a plurality of cutting elements protruding therefrom, the reciprocal output from the motor reciprocating both the shaft and the circular base member.

10. The apparatus of claim 9 wherein the cutter elements taper to a point in a direction from the base member.

11. The apparatus of claim 9 wherein the motor is a variable speed brushless dc motor configured to produce the reciprocal output.

12. The apparatus of claim 9 further comprising a collet mounted to the arm and coupled between the motor and the cutter bit to reciprocate the cutter bit upon activation of the motor.

13. The apparatus of claim 9 wherein the arm is pivotally mounted to the pedestal to allow a vessel containing the segments to be positioned under the cutter bit.

14. The apparatus of claim 9, wherein the cutter elements taper to a point in a direction from the base member, the cutter elements at the base member being spaced apart from each other along the lower surface of the base member.

15. The apparatus of claim 9, wherein the cutter elements have a greatest width adjacent the base member and taper in a direction from the base member, the cutter elements being spaced apart from each other such that a portion of the lower surface is disposed between adjacent cutter elements.

16. The apparatus of claim 9, wherein the cutter elements have a greatest width adjacent the base member and a height from the lower surface of the base member, the height being a distance about twice the greatest width.

17. A method for morselizing bone segments:
mounting a cutter bit to a casing, the cutter bit having a longitudinally extending shaft and having a circular base member fixed relative to the shaft, the circular base member having a lower surface defining a plane substantially normal to the longitudinally extending shaft with a plurality of cutting elements protruding therefrom;
manually grasping the casing and positioning it over a plurality of the segments;
activating a motor to cause reciprocation of both the shaft and the circular base member of the cutter bit; and
impacting the segments with the cutter bit to morselize the segments.

18. The method of claim 17 further comprising mounting the motor in the casing, and coupling the output shaft of the motor to the cutter bit.

19. A method for morselizing bone segments comprising:
mounting an arm to a pedestal;
mounting a cutter bit to an arm, the cutter bit having a longitudinally extending shaft and having a circular base member fixed relative to the shaft, the circular base member having a lower surface defining a plane substantially normal to the longitudinally extending shaft with a plurality of cutting elements protruding therefrom;
positioning a vessel containing bone segments under the cutter bit;
activating a motor to cause reciprocation of both the shaft and the circular base member of the cutter bit; and
impacting the segments with the cutter bit to morselize the segments.

20. The method of claim 19 further comprising mounting the motor in the arm or the pedestal and coupling the output shaft of the motor to the cutter bit.

* * * * *